(12) United States Patent
Fitz (10) Patent No.: US 10,350,094 B2
(45) Date of Patent: Jul. 16, 2019

(54) IMPLANTABLE DEVICE WITH ADHESIVE PROPERTIES

(71) Applicant: MicroVention, Inc., Aliso Viejo, CA (US)

(72) Inventor: Matthew J. Fitz, Vista, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 365 days.

(21) Appl. No.: 14/201,634

(22) Filed: Mar. 7, 2014

(65) Prior Publication Data

US 2014/0257320 A1    Sep. 11, 2014

Related U.S. Application Data

(60) Provisional application No. 61/776,468, filed on Mar. 11, 2013.

(51) Int. Cl.
*A61B 17/12* (2006.01)
*A61F 2/848* (2013.01)
(Continued)

(52) U.S. Cl.
CPC .......... *A61F 2/848* (2013.01); *A61B 17/1215* (2013.01); *A61B 17/12113* (2013.01);
(Continued)

(58) Field of Classification Search
CPC .... A61F 2/848; A61F 6/20; A61F 6/22; A61F 2/88; A61F 2/885; A61B 17/1215; A61B 17/12177; A61B 2017/12109; A61B 2017/12113; A61B 17/12027; A61B 17/12031; A61B 17/12036; A61B 17/1204; A61B 17/12045; A61B 17/12099; A61B 17/12104; A61B 17/12109; A61B 17/12113; A61B 17/12118; A61B 17/12122; A61B 17/12168; A61B 17/12186; A61B 17/1219;
(Continued)

(56) References Cited

U.S. PATENT DOCUMENTS 3,969,552 A  7/1976 Malofsky et al.
3,973,556 A  8/1976 Fleischhacker et al.
(Continued)

FOREIGN PATENT DOCUMENTS

CN  1250382 A  4/2000
EP  0652026 A1  11/1993
(Continued)

OTHER PUBLICATIONS

Fountain, Henry; "Studying Sea Life for a Glue That Mends People"; Apr. 12, 2010; The New York Times; pp. 1-4; http://www.nytimes.com/2010/04/13/science/13adhesive.html?_r=0&src=sch&pagewanted=print.*
(Continued)

*Primary Examiner* — Ryan J. Severson
*Assistant Examiner* — Christian D. Knauss
(74) *Attorney, Agent, or Firm* — Inskeep IP Group, Inc.

(57) ABSTRACT

Implantable devices such as stents, coils, implantable contraceptives, vascular plugs, vena cava filters, left atrial appendage (LAA) closure devices employing an adhesive component to assist in securing or holding the implant in place within a lumen of a patient's body.

17 Claims, 5 Drawing Sheets

(51) Int. Cl.
*A61F 6/00* (2006.01)
*A61F 6/20* (2006.01)
*A61B 17/00* (2006.01)

(52) U.S. Cl.
CPC .. *A61B 17/12177* (2013.01); *A61B 17/12186* (2013.01); *A61F 6/00* (2013.01); *A61F 6/20* (2013.01); *A61B 17/00491* (2013.01); *A61B 2017/1205* (2013.01); *A61F 2220/005* (2013.01); *A61F 2220/0008* (2013.01); *A61F 2310/00389* (2013.01); *Y10T 428/13* (2015.01); *Y10T 428/249955* (2015.04); *Y10T 428/28* (2015.01)

(58) Field of Classification Search
CPC ...... A61B 17/12195; A61B 2017/1205; A61B 2017/12054; A61B 2017/12059; A61B 2017/12063; A61B 2017/12068; A61B 2017/12081; A61B 2017/12086; A61B 2017/1209; A61B 2017/12095
See application file for complete search history.

(56) References Cited

U.S. PATENT DOCUMENTS

| | | | |
|---|---|---|---|
| 4,003,369 A | 1/1977 | Heilman et al. | |
| 4,147,821 A | 4/1979 | Young | |
| 4,263,372 A | 4/1981 | Emmons et al. | |
| 4,435,476 A | 3/1984 | Phillips et al. | |
| 4,504,528 A | 3/1985 | Zucker et al. | |
| 4,541,980 A | 9/1985 | Kiersarsky et al. | |
| 4,556,701 A | 12/1985 | Schindler et al. | |
| 4,705,584 A | 11/1987 | Lauchenauer | |
| 4,729,914 A | 3/1988 | Kliment et al. | |
| 4,784,159 A | 11/1988 | Szilagyi | |
| 4,795,472 A | 1/1989 | Crowninshield et al. | |
| 5,041,090 A * | 8/1991 | Scheglov | A61B 17/12022 604/101.02 |
| 5,095,915 A | 3/1992 | Engelson | |
| 5,129,890 A | 7/1992 | Bates et al. | |
| 5,217,026 A | 6/1993 | Stoy et al. | |
| 5,235,964 A | 8/1993 | Abenaim | |
| 5,290,585 A | 3/1994 | Elton | |
| 5,331,027 A | 7/1994 | Whitbourne | |
| 5,333,620 A | 8/1994 | Moutafis et al. | |
| 5,437,288 A | 8/1995 | Schwartz et al. | |
| 5,441,488 A | 8/1995 | Shimura et al. | |
| 5,443,455 A | 8/1995 | Hergenrother et al. | |
| 5,443,907 A | 8/1995 | Slaikeu et al. | |
| 5,573,520 A | 11/1996 | Schwartz et al. | |
| 5,700,559 A | 12/1997 | Sheu et al. | |
| 5,741,429 A | 4/1998 | Donadio, III et al. | |
| 5,746,701 A | 5/1998 | Noone | |
| 5,749,968 A | 5/1998 | Melanson et al. | |
| 5,750,206 A | 5/1998 | Hergenrother et al. | |
| 5,833,632 A | 11/1998 | Jacobsen et al. | |
| 5,840,046 A | 11/1998 | Deem | |
| 5,891,057 A | 4/1999 | Chaisson et al. | |
| 5,902,631 A | 5/1999 | Wang et al. | |
| 5,984,878 A | 11/1999 | Engelson | |
| 5,997,517 A | 12/1999 | Whitbourne | |
| 6,024,754 A * | 2/2000 | Engelson | A61B 17/12022 128/898 |
| 6,027,863 A | 2/2000 | Donadio, III | |
| 6,033,394 A | 3/2000 | Vidlund et al. | |
| 6,080,488 A | 6/2000 | Hostettler et al. | |
| 6,086,548 A | 7/2000 | Chaisson et al. | |
| 6,110,164 A | 8/2000 | Vidlund | |
| 6,149,681 A * | 11/2000 | Houser | A61F 2/07 623/1.12 |
| 6,149,978 A | 11/2000 | Bladel et al. | |
| 6,162,310 A | 12/2000 | Tseng | |
| 6,176,849 B1 | 1/2001 | Yang et al. | |
| 6,224,626 B1 * | 5/2001 | Steinke | A61L 31/022 623/1.16 |
| 6,296,632 B1 * | 10/2001 | Luscher | A61B 17/12022 604/264 |
| 6,379,329 B1 * | 4/2002 | Naglreiter | A61B 17/12113 604/101.02 |
| 6,408,213 B1 | 6/2002 | Bartig et al. | |
| 6,530,934 B1 * | 3/2003 | Jacobsen | A61B 17/12022 606/157 |
| 6,786,876 B2 | 9/2004 | Cox | |
| 6,878,384 B2 | 4/2005 | Cruise et al. | |
| 7,494,687 B2 | 2/2009 | Cox | |
| 2002/0198601 A1 | 12/2002 | Bales et al. | |
| 2004/0091543 A1 * | 5/2004 | Bell | A61B 17/12022 424/489 |
| 2004/0138697 A1 * | 7/2004 | West | A61B 17/12022 606/200 |
| 2005/0015140 A1 * | 1/2005 | deBeer | A61B 17/68 623/1.21 |
| 2005/0125034 A1 * | 6/2005 | Cichocki, Jr. | A61B 17/06166 606/222 |
| 2005/0196426 A1 | 9/2005 | Cruise et al. | |
| 2005/0209636 A1 * | 9/2005 | Widomski | A61B 17/0057 606/213 |
| 2006/0271099 A1 * | 11/2006 | Marks | A61B 17/12022 606/200 |
| 2007/0233188 A1 * | 10/2007 | Hunt | A61B 17/00234 606/228 |
| 2008/0033522 A1 | 2/2008 | Grewe et al. | |
| 2008/0195196 A1 * | 8/2008 | Asgari | A61F 2/856 623/1.39 |
| 2009/0112237 A1 * | 4/2009 | Paul, Jr. | A61F 2/06 606/155 |
| 2010/0256064 A1 * | 10/2010 | Woolfson | A61B 17/205 514/15.2 |
| 2011/0046658 A1 * | 2/2011 | Connor | A61B 17/12022 606/200 |
| 2011/0190870 A1 * | 8/2011 | Hastings | A61F 2/82 623/1.15 |
| 2011/0245906 A1 | 10/2011 | DiMatteo et al. | |
| 2012/0245663 A1 | 9/2012 | Zarembo et al. | |
| 2012/0303052 A1 * | 11/2012 | Connor | A61B 17/12113 606/194 |

FOREIGN PATENT DOCUMENTS

| | | |
|---|---|---|
| EP | 0680351 B1 | 8/1998 |
| JP | 04-232332 A | 8/1992 |
| JP | 6-35740 U | 5/1994 |
| JP | 2000-107296 A | 4/2000 |
| JP | 2000513235 A | 10/2000 |
| WO | WO1992/011877 A1 | 7/1992 |
| WO | WO1993/004722 A2 | 3/1993 |
| WO | WO1996/038193 A1 | 12/1996 |
| WO | WO1998/032474 A1 | 7/1998 |
| WO | WO2000/006239 A1 | 2/2000 |
| WO | WO2000/065143 A1 | 11/2000 |
| WO | WO2003/000116 A2 | 1/2003 |

OTHER PUBLICATIONS

WIPO, International Preliminary Examining Authority (U.S. Patent and Trademark Office), International Preliminary Report on Patentability dated Sep. 24, 2015 in International Patent Application No. PCT/US2014/022108, 6 pages.
WIPO, U.S. International Search Authority, International Search Report and Written Opinion dated Jun. 17, 2014 in International Patent Application No. PCT/US2014/022108, 8 pages.
European Patent Office, Decision to Grant dated Jul. 8, 2008 in European Patent Application No. EP02744542.8-2305, 24 pages.
Japan Patent Office, Official Action dated Aug. 5, 2008 in Japanese Patent Application Serial No. 2003-506750 with English translation, 8 pages.
IP Australia, Notice of Acceptance dated Dec. 18, 2007 in Australian Patent Application No. 2002345795, 3 pages.
European Patent Office, Examination Report dated Jul. 27, 2007 in European Patent Application No. EP02744542.8-1219, 2 pages.

(56) References Cited

OTHER PUBLICATIONS

European Patent Office, Examination Report dated Dec. 5, 2005 in European Patent Application No. EP02744542.8-1219, 5 pages.
European Patent Office, Supplementary European Search Report dated Aug. 4, 2005 in European Patent Application No. EP02744542.8-2107, 3 pages.
WIPO, International Preliminary Examining Authority (U.S. Patent and Trademark Office), International Preliminary Examination Report dated Jun. 5, 2003 in International Patent Application No. PCT/US2002/019833, 3 pages.
WIPO, U.S. International Search Authority, International Search Report published in International Patent Application No. PCT/US2002/019833, 3 pages.

* cited by examiner

IMPLANTABLE DEVICE WITH ADHESIVE PROPERTIES

RELATED APPLICATIONS

This application claims priority to U.S. Provisional Application Ser. No. 61/776,468 filed Mar. 11, 2013 entitled Implantable Device with Adhesive Properties, which is hereby incorporated herein by reference in its entirety.

FIELD OF THE INVENTION

The present invention relates generally to the field of implantable devices and, more particularly, to implantable devices employing an adhesive or adhesion promoting structural features for enhanced adhesion of the implantable device to body tissue and/or to other implantable devices.

BACKGROUND OF THE INVENTION

It is often necessary to place an implantable device within a body of a patient. For example, it may be necessary to place a stent within a body duct or blood vessel, a coil within a malformation such as an aneurysm, or a contraceptive device within a fallopian tube of a patient. It is possible that the implant may undesirably move or migrate after deployment of the device at the target location. To lessen the risk of such undesirable movement, mechanical fixation components and techniques, such as hooks or staples, may be employed to couple the device to patient tissue. In aneurysm treatment, intravascular stents have been used to block coils deployed within the aneurysm from migration out of the aneurysm.

Such mechanical fixation components and techniques have the disadvantage of increasing the risk that the patient tissue to which the fixation is made will be damaged. Hence, there is a need in the field for devices and methods for decreasing the risk of migration or movement of implantable devices that do not increase the risk of causing patient tissue damage.

SUMMARY OF THE INVENTION

The present invention employs implantable devices having adhesive properties in order to assist in holding or securing one or more implantable devices in the desired position within a patient's body. According to the present invention, implantable devices, such as stents, coils, implantable contraceptives, vascular plugs, vena cava filters, left atrial appendage (LAA) closure devices, utilize adhesives and/or adhesive properties or adhesive promoting structure to hold or secure the implantable devices in place within the patient's body, for example within a patient's vasculature, body duct, or fallopian tube.

In one embodiment of the present invention an implantable device utilizes an adhesive coating or adhesive surface.

In another embodiment of the present invention an implantable device utilizes an adhesive that adheres or sticks selectively only to another implant or another adhesive.

In another embodiment of the present invention an implantable device utilizes a semi-permeable or permeable lumen through which an adhesive is employed.

In another embodiment of the present invention an implantable device utilizes one or more semi-permeable or permeable compartments formed in a surface of the implantable device, for example formed in an exterior or interior surface of the device.

In another embodiment of the present invention an implantable device utilizes an adhesive which is pre-sealed or temporarily contained within a lumen or compartment of the implantable device.

In another embodiment of the present invention an adhesive is delivered to a lumen or compartment of the implantable device by an injection port.

In another embodiment of the present invention an adhesive is delivered to a lumen or compartment of the implantable device by an injection port and a heater is employed to detach the lumen from the implantable device.

In another embodiment of the present invention an implantable device has one or more flow channels, and an adhesive is delivered to the one or more flow channels by and injection port.

In another embodiment of the present invention an implantable device employs structural features, for example surface structure features, that impart non-chemical adhesion properties for retention of the implantable device within a patient's body, for example within a patient's vasculature, body duct, or fallopian tube.

BRIEF DESCRIPTION OF THE DRAWINGS

These and other aspects, features and advantages of the invention will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Broadly speaking, the present invention provides devices and methods for holding and/or securing an implantable device within a lumen of a patient, for example within a patient's vasculature, fallopian tube, or other duct. These advantages are achieved by providing implantable devices that employ an adhesive component in the form of a chemical adhesive and/or adhesion promoting structural features and methods for preparing and implanting the same. The adhesive component of the implantable device enhances adhesion of the implantable device to a patient body tissue and/or to the other implantable devices.

With reference to FIGS. 1-4, in one embodiments of the present invention the implantable device or implant 10 employs an adhesive component in the form of an chemical adhesive 12 that is coated, printed, or otherwise applied on an exterior surface of the implant 10. The implantable device 10 may, for example, be a coil, stent, stent-graft, and/or filter. For the sake of clarity and by way of example, FIGS. 1-4 show the generally tubular shape implants 10 in cross-section. The tubular implants are formed of one or more struts 14 that are manipulated into a coil or weave. The struts 14 are formed of one or more metal, alloy, or polymeric wires or filaments. Alternatively, such tubular shaped implants 10 are formed from of a preformed metal, alloy, or polymeric tubular element that is subsequently manipulated by laser or other form of cutting so as to form struts 14 that define apertures or windows 18 within the tubular form of the implant 10.

Figure 1:
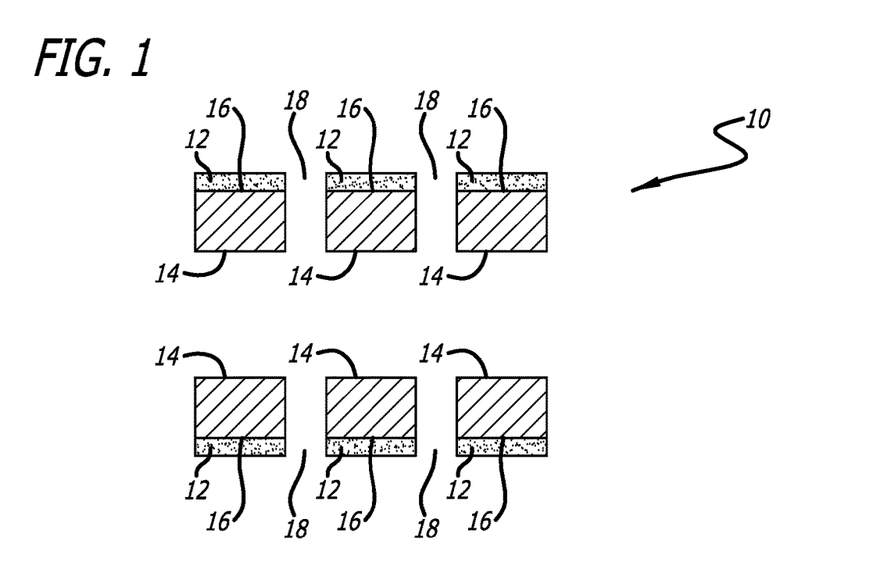
FIG. 1 is a cross-sectional view of a portion of an implantable device with an adhesive coating according to certain embodiments of the present invention.
Figure 2:
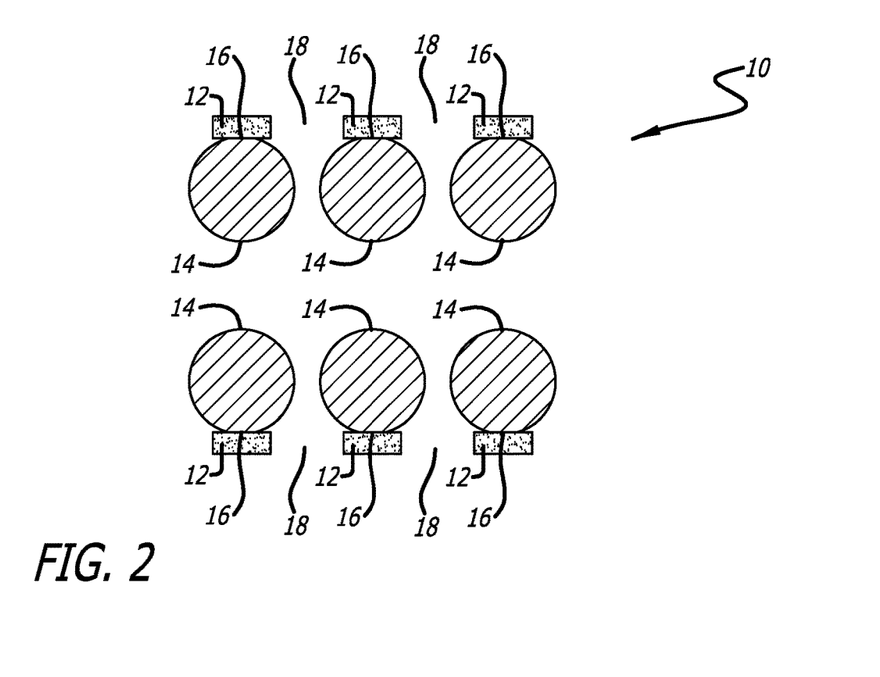
FIG. 2 is a cross-sectional view of a portion of an implantable device with an adhesive coating according to certain embodiments of the present invention.

FIG. 1 shows a cross-sectional view of a portion of the implant 10 formed of struts 14 having rectangular or non-circular cross-sections. FIG. 2 shows a cross-sectional view of a portion of the implant 10 formed of struts 14 having circular or oval cross-sections. The adhesive 12 is coated, printed, or otherwise applied on an exterior surface 16 of the struts 14 of the implants 10.

Figure 3:
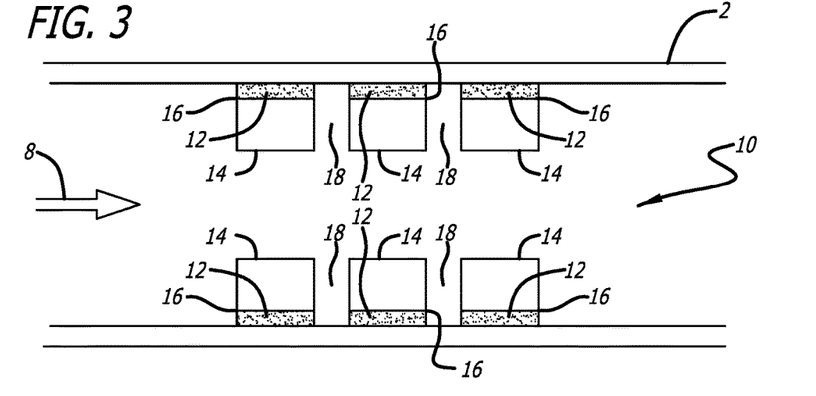
FIG. 3 is a cross-sectional view of a portion of an implantable device with an adhesive coating according to certain embodiments of the present invention within a blood vessel.
Figure 4:
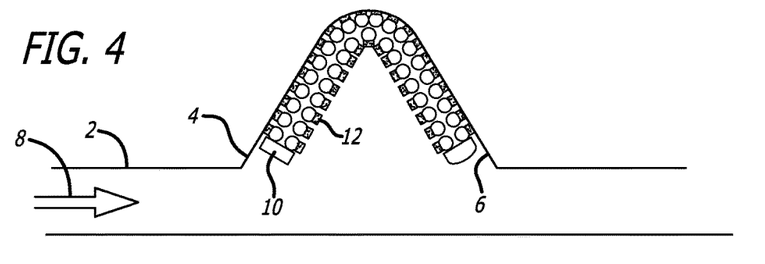
FIG. 4 is a cross-sectional view of an implantable device with an adhesive coating according to certain embodiments of the present invention within an aneurysm.

FIG. 3 shows a cross-sectional view of a portion of the implant 10 of FIG. 1 deployed within a lumen of patient, for example, deployed within a patient's vasculature 2. The direction of a flow of blood within the vasculature 2 is indicated by arrow 8. FIG. 4 shows a cross-sectional view of an implant 10, such as the implant 10 of FIG. 2, deployed within an aneurysm 4 of a patient's vasculature 2.

The adhesive 12 is, for example, an adhesive material such as n-butyl cyanoacrylate (nBCA), a protein with adhesive properties such as the secretion of a sandcastle marine worm, or a siloxane system such as that described in Wilson et al., Biomater Sci Polymer Ed. 2005; 16(4): 449-72, which is hereby incorporated by reference in its entirety. In general, it may be advantageous to use an adhesive 12 that is reactive to temperature, pH, salinity, water, or other biological factors in order to facilitate delivery of the implant 10 into the patient's body in a non- or lower-adhesive state. Upon delivery and/or deployment of the implant 10 to the target location, the adhesive strength of the adhesive 12 increases due to, at least in part, the reactivity of the adhesive 12 to a temperature, pH, salinity, water content, or other biological factor(s) present at the target location.

The adhesive can advantageously comprise a radiopaque material such as barium sulfate, tantalum powder, or iodine contrast solution so as to allow an operator to better visualize the implant 10.

The adhesive 12 is, for example, applied to the implant 10 by dipping, spraying, painting, printing or other processes known in the art. Once the adhesive 12 is applied, the implant 10 is then delivered through an implant delivery system employing, for example, a sheath or catheter and an implant detachment component. Upon deployment, the adhesive 12 of the implant 10 enhances fixation or securing of the implant 10 in the target location, thereby reducing the probability of undesirable migration of the implant 10 from the target location.

In certain embodiments of the present invention, an adhesive 12 is selected that adheres selectively only to itself, self-adhering, and/or adheres selectively to a metal, alloy, or polymeric material of a non-adhesive implant, i.e. an implant that does not employ the adhesive 12. Employing an adhesive 12 that is only or primarily self-adhering or that is selectively adhering to another implant is advantageous where multiple implants are used for treatment at a single target location, for example, for treatment of aneurysms with multiple coil implants.

Figure 5A:
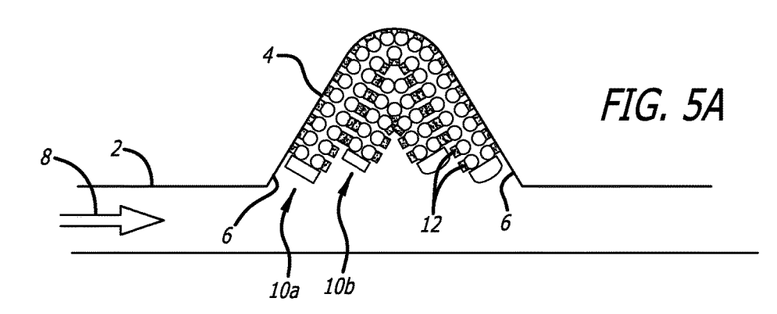
FIG. 5A is a cross-sectional view of an implantable device with an adhesive coating according to certain embodiments of the present invention within an aneurysm.
Figure 5B:
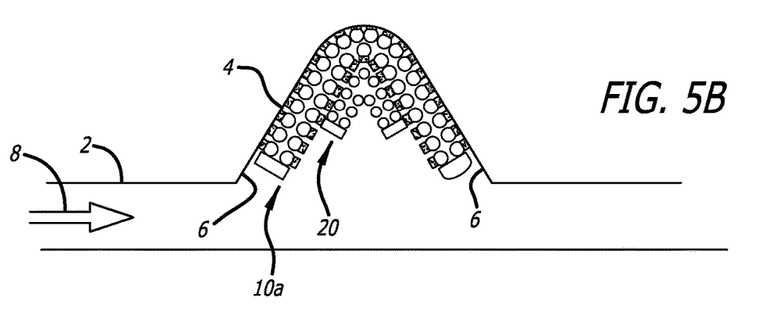
FIG. 5B is a cross-sectional view of an implantable device with an adhesive coating according to certain embodiments of the present invention within an aneurysm.

By way of example, according to the present embodiment, FIG. 5A shows an implant 10a employing an adhesive 12 that is deployed within an aneurysm 4. Wherein a gap or space between the adhesive 12 of the implant 10a and an interior surface 6 of the aneurysm 4 depicts a lack of adhesion of the adhesive 12 to the interior surface 6 of the aneurysm 4. In contrast, the absence of a gap or space between the adhesive 12 of the implant 10a and an implant 10b depicts the presence of adhesion between the adhesive 12 of the implant 10a and the adhesive 12 of the implant 10b. FIG. 5B shows an implant 10a employing an adhesive 12 that is deployed within an aneurysm 4. Wherein a gap or space between the adhesive 12 of the implant 10a and an interior surface 6 of the aneurysm 4 depicts a lack of adhesion of the adhesive 12 to the interior surface 6 of the aneurysm 4. In contrast, the absence of a gap or space between the adhesive 12 of the implant 10a and a non-adhesive implant 20 depicts the presence of adhesion between the implant 10a and the implant 20.

The presence of a plurality of self-adhering or selectively-adhering implants at the target location adhered to one another creates a more stable mass and, thereby, prevents the plurality of implants from shifting or migrating from the target location over time. The present embodiment is also advantageous in treatment situations where there may be a need to reposition the implant and/or where there is a possibility of tearing the tissue at the target location if the implant adheres to such tissue.

The adhesive 12 is, for example, an adhesive material such as n-butyl cyanoacrylate (nBCA), a protein with adhesive properties such as the secretion of a sandcastle marine worm, or a siloxane system such as that described in Wilson et al., Biomater Sci Polymer Ed. 2005; 16(4): 449-72, which is hereby incorporated by reference in its entirety. In general, it may be advantageous to use an adhesive 12 that is reactive to temperature, pH, salinity, water, or other biological factors in order to facilitate delivery of the implant 10 into the patient's body in a non- or lower-adhesive state. Upon delivery and/or deployment of the implant 10 to the target location, the adhesive strength of the adhesive 12 increases due to, at least in part, the reactivity of the adhesive 12 to a temperature, pH, salinity, water content, or other biological factor(s) present at the target location.

Figure 6:
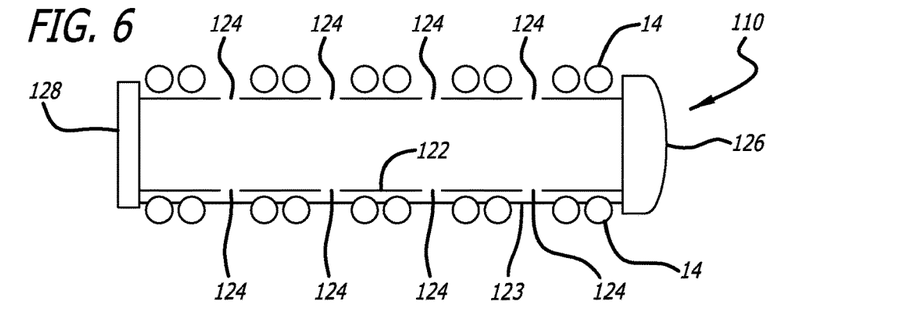
FIG. 6 is a cross-sectional view of an implantable device with an adhesive coating according to certain embodiments of the present invention.
Figure 7:
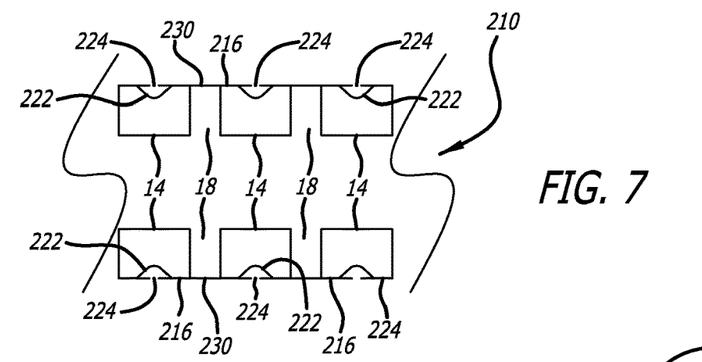
FIG. 7 is a cross-sectional view of a portion of an implantable device according to certain embodiments of the present invention.

With reference to FIGS. 6 and 7, in another embodiment of the present invention, an implant employs an adhesive that is temporarily and/or is semi-sealed within a portion of the implant, for example within one or more lumens or cavities formed within the implant, prior to delivery and deployment of the implant to a target location within a patient. The one or more lumens or cavities are semi-permeable to an exterior surface of the implant such that, upon deployment of the implant at the target location, the adhesive within the one or more lumens or cavities will diffuse or migrate to an exterior surface of the implant. Once at the surface, the adhesive will adhere the implant to the patient's tissue, to other implants, and/or both, and thereby assist in securing the implant at the target location. Since many adhesives such as nBCA and sandcastle-worm adhesive solidify and harden as they cure, the mechanical properties of the implant will change, thereby providing additional stability and resistance against migration or movement of the implant.

More particularly, with reference to FIG. 6, in certain embodiments of the present invention, the adhesive 12 is pre-loaded into at least one lumen 122 formed within an implant 110 having pores or holes 124 formed therein. The size or diameter of the pores or holes 124 of the lumen 122 are selected so as to selectively control a diffusion rate of the adhesive 12 from the lumen 122. Hence, the time in which the adhesive 12 adheres the implant 110 to the tissue and/or to other implants is controlled so as to allow an operator to deliver, deploy, and re-position the implant 110 at the target location prior to adhesion of the implant 110 to the tissue and/or to other implants. The diffusion rate may alternatively or additionally, be controlled by treating an exterior surface of the lumen 122 with a dissolvable substance such as salt. In order for the adhesive 12 to diffuse or migrate from the interior of the lumen 122, the dissolvable substance is first dissolved from the surface to the lumen 122 by patient fluids, such as blood.

The lumen 122 is formed, for example, of a polyolefin or ethylene-octene copolymer extruded under conditions resulting in the formation of micropores within the extrusion. Alternatively, the lumen 122 is formed from a polyamide that has micro-holes cut therein by an excimer laser or other cutting technique. Alternatively, the lumen 122 is formed from a polymer such as a polyolefin, Teflon, polyamide, PEEK, PET, or the like with holes cut with an appropriately sized needle or drill.

The adhesive 12 employed in the implant 110 is, for example, an adhesive material such as n-butyl cyanoacrylate (nBCA), a protein with adhesive properties such as the secretion of a sandcastle marine worm, or a siloxane system such as that described in Wilson et al., Biomater Sci Polymer Ed. 2005; 16(4): 449-72, which is hereby incorporated by reference in its entirety. In general, it may be advantageous to use an adhesive 12 that is reactive to temperature, pH, salinity, water, or other biological factors in order to facilitate delivery of the implant 10 into the patient's body in a non- or lower- adhesive state. Upon delivery and/or deployment of the implant 110 to the target location, the adhesive strength of the adhesive 12 increases due to, at least in part, the reactivity of the adhesive 12 to a temperature, pH, salinity, water content, or other biological factor(s) present at the target location.

The adhesive 12 can advantageously comprise a radiopaque material such as barium sulfate, tantalum powder, or iodine contrast solution so as to allow an operator to better visualize implant 110.

In one illustrative example, shown in FIG. 6, the implant 110 for treating an aneurysm has a primary shape formed from a coil having an outer diameter, OD, of approximately 0.012 inches and an inner diameter, ID, of approximately 0.008 inches and a secondary shape formed by further winding or manipulating the primary shape. The lumen 122 is formed of a polymer tube made from, for example, a polyolefin elastomer having a 0.007 inch OD and a 0.005 inch ID that is threaded through the 0.008 inch ID of the primary shape or coil of the implant 110. The lumen 122 has multiple holes of approximately 0.0001-0.001 inches in diameter formed therein. The implant 110 is then dipped into a salt solution and cured so that a salt coating 123 at least partially blocks some of the holes 124 of the lumen 122. A distal portion of the lumen 122 is then closed or sealed by employing a knot or bonding near a distal end 126 of the primary shape of the implant 110.

The adhesive 12, for example, nBCA or sandcastle-worm secretion, is then injected into an open proximal end of the lumen 122 while the lumen 122 is maintained in an approximately vertical position, thereby, at least partially filling the lumen 122 with adhesive 12. A proximal portion of the lumen 122 near a proximal end 128 of the primary shape of the implant 110 is tied or bonded such that the adhesive 12 is at least partially or temporarily sealed within the lumen 122 of the implant 110. The above-described lumen 122 and manufacturing steps have the additional benefit of enhancing the stretch-resistance of the implant 110. The proximal end 128 of the completed implant 110 is then attached to a distal portion of a delivery mechanism.

Using the delivery mechanism, the implant 110 is then intravenously delivered into an aneurysm or other body cavity using components such as a microcatheter. Once in contact with blood, the salt coating 123 of the implant 110 begins to wash away and/or dissolve, thereby opening the holes 124 in the lumen 122, allowing blood to infiltrate into the lumen 122, and allowing the adhesive 12 to diffuse or migrate from an interior of the lumen 122 to the exterior surface of the implant 110. During this time, which may be from 1 to 60 minutes, if desired, the operator can reposition the implant 110 with in the target location. Once the adhesive 12 reaches the exterior surface of the implant 110, the adhesive 12 will contact patient tissue, other implants, and/or both and adhere the implant 110 to the patient tissue, other implants, and/or both. Hence, the implant 110 will be held in the target location and the risk of migration of the implant 110 will be reduced.

In another embodiment, with reference to FIG. 7, the adhesive 12 is pre-loaded, i.e. loaded prior to delivery to a target location within the patient, into one or more wells 222 formed into an exterior surface 216 of the implant 210. The wells 222 are formed, for example, by machining, drilling, etching, or similar means. After formation of the wells 222, the wells 222 are enclosed with a covering 230 having pores or holes 224. Once the wells 222 have been covered by the cover 230, the adhesive 12 is injected or otherwise placed within the wells 222.

The size or diameter of the pores or holes 224 of the covering 230 are selected so as to selectively control the diffusion rate of the adhesive 12 from the wells 222. Hence, the time in which the adhesive 12 adheres the implant 210 to the tissue and/or to other implants controlled so as to allow an operator to deliver, deploy, and re-position the implant 210 at the target location prior to adhesion of the implant 210 to the tissue and/or to other implants. The diffusion rate may alternatively or additionally, be controlled by treating an exterior surface of the covering 230 with a dissolvable substance such as salt. In order for the adhesive 12 to diffuse or migrate from the interior of the covering 230, the dissolvable substance is first dissolved from the surface to the covering 230 by patient fluid, such as blood.

The covering 230 is formed, for example, of a polymer such as a UV curable polymer and pores or holes 224 are formed therein as previously described. Alternatively, the covering 230 is formed of, for example, a polyolefin or ethylene-octene copolymer extruded under conditions resulting in the formation of micropores 224 within the extrusion. Alternatively, the covering 230 is formed from a polyamide that has micro-holes 224 cut therein by an excimer laser or other cutting technique. Alternatively, the covering 230 is formed from a polymer such as a polyolefin, Teflon, polyamide, PEEK, PET, or the like with holes 224 cut with an appropriately sized needle or drill.

The adhesive 12 employed in the implant 210 is, for example, an adhesive material such as n-butyl cyanoacrylate (nBCA), a protein with adhesive properties such as the secretion of a sandcastle marine worm, or a siloxane system such as that described in Wilson et al., Biomater Sci Polymer Ed. 2005; 16(4): 449-72, which is hereby incorporated by reference in its entirety. In general, it may be advantageous to use an adhesive 12 that is reactive to temperature, pH, salinity, water, or other biological factors in order to facilitate delivery of the implant 210 into the patient's body in a non- or lower-adhesive state. Upon delivery and/or deployment of the implant 210 to the target location, the adhesive strength of the adhesive 12 increases due, at least in part, to the reactivity of the adhesive 12 to a temperature, pH, salinity, water content, or other biological factor(s) present at the target location.

The adhesive can advantageously comprise a radiopaque material such as barium sulfate, tantalum powder, or iodine contrast solution so as to allow an operator to better visualize implant 210.

In one illustrative example, the implant 210 employs wells 222, such as those disclosed in U.S. Pat. No. 7,208,011 to Shanley which is hereby incorporated by reference in its entirety. The wells 222 are filled with adhesive such as nBCA or sandcastle-worm adhesive and covered or sealed with the cover 230 formed of either a biodegradable polymer as described by Shanley or the permeable cover 230 previously disclosed that need not be biodegradable. Advantageously, the holes 224 are sealed with a material such as salt or sugar that quickly dissolves in a matter of a few minutes and/or that would allow relatively quick diffusion to ensure reliable adhesion of the implant 210 to the tissue. After delivery, the seal degrades and allows the adhesive 12 to diffuse to the surface of the implant 210 so as to adhere the implant 210 to patient tissue, other implants, and/or both.

The operation and method for delivery and deployment of the implant 210 is otherwise as previously described with respect to implant 110.

With reference to Figs. 8-11, in another embodiment of the present invention, an implant employs an adhesive that is delivered through a portion of the implant, for example through one or more lumens or cavities formed within the implant, after delivery and deployment of the implant at a target location within a patient. In order to deliver the adhesive to the implant, after delivery and deployment of the implant at a target location, the implant is partially integrated with a portion of a delivery system so as to form a delivery passage or lumen for flow of the adhesive. The one or more lumens or cavities of the implant are semi-permeable to an exterior surface of the implant such that, upon delivery of the adhesive to the implant at the target location, the adhesive within the one or more lumens or cavities will diffuse or migrate to the exterior surface of the implant. Once at the surface, the adhesive will adhere the implant to the patient's tissue, to other implants, and/or both, and thereby assist in securing the implant at the target location. The present embodiment allows an operator to deliver and re-position as needed and introduce the adhesive 12 only when the operator desires.

Figure 8:
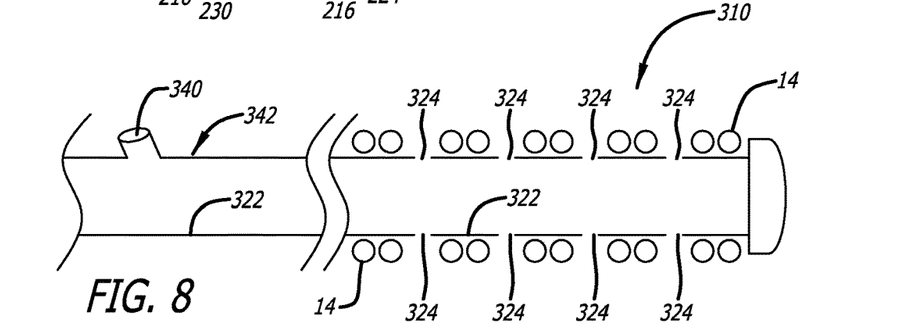
FIG. 8 is a cross-sectional view of a portion of an implantable device according to certain embodiments of the present invention.

More particularly, with reference to FIG. 8, in certain embodiments of the present invention, a lumen 322 extends through at least a portion of an implant 310 and through at least a portion of a delivery system 342 to an injection port 340. The lumen 322 may be formed of a contiguous tube or may be formed of a series of interconnected tubes with or without differing mechanical properties. Such systems are described in U.S. Pat. Nos. 6,689,141 and 6,607,538, and U.S. Publication Nos. 2002/0188311 and US2004/0204701, all of which are hereby incorporated by reference in their entirety. At least a portion of the lumen 322 within the implant 310 has pores or holes 324 formed therein. The size or diameter of the pores or holes 324 of the lumen 322 is selected so as to selectively control the diffusion or migration of the adhesive 12 from the lumen 322. The previously described step of salt-treating the surface of the lumens 110 and 210 may not be necessary since no adhesive 12 is present in the lumen at the time of delivery and deployment of the implant 310.

The lumen 322 is formed from a polyamide that has micro-holes cut therein by an excimer laser or other cutting technique. Alternatively, the lumen 322 is formed from a polymer such as a polyolefin, Teflon, polyamide, PEEK, PET, or the like with holes cut with an appropriately sized needle or drill.

The adhesive 12 employed in the implant 310 is, for example, an adhesive material such as n-butyl cyanoacrylate (nBCA), a protein with adhesive properties such as the secretion of a sandcastle marine worm, or a siloxane system such as that described in Wilson et al., Biomater Sci Polymer Ed. 2005; 16(4): 449-72, which is hereby incorporated by reference in its entirety. In general, it may be advantageous to use an adhesive 12 that is reactive to temperature, pH, salinity, water, or other biological factors in order to facilitate delivery of the implant 310 into the patient's body in a non-or lower-adhesive state. Upon delivery and/or deployment of the implant 310 to the target location, the adhesive strength of the adhesive 12 increases due to, at least in part, the reactivity of the adhesive 12 to a temperature, pH, salinity, water content, or other biological factor(s) present at the target location.

The adhesive 12 can advantageously comprise a radiopaque material such as barium sulfate, tantalum powder, or iodine contrast solution so as to allow an operator to visualize the adhesive as it is delivered through the delivery system 342.

Prior to use, the lumen 322 may be flushed of air by, for example, injecting saline solution through the injection port 340. The operator will then deliver and reposition the implant 310 until the desired placement is achieved. Prior to detaching the implant 310 from the delivery system 342, the adhesive 12 is injected through the injection port 340. Injection of the adhesive 12 displaces the saline solution within the lumen 322. The adhesive is pushed or wick out of the holes 324 in the lumen 322 and to the surface of the implant 310. Once the adhesive 12 reaches the surface of the implant 310, the adhesive 12 will contact patient tissue, other implants, and/or both and adhere the implant 310 to the patient tissue, other implants, and/or both. Hence, the implant 310 will be held in the target location and the risk of migration of the implant 310 will be reduced.

Figure 9:
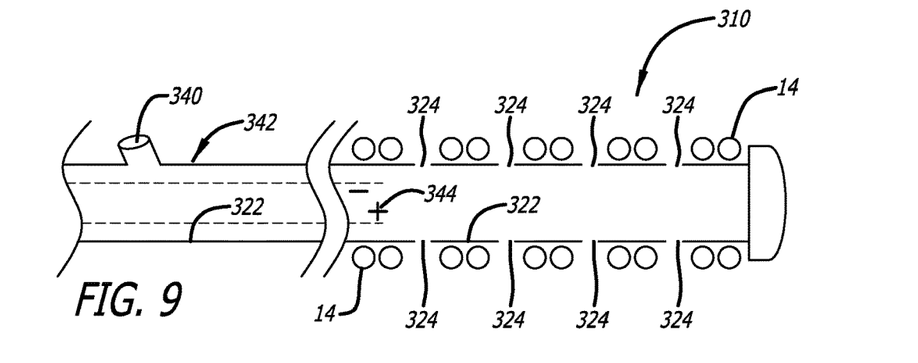
FIG. 9 is a cross-sectional view of a portion of an implantable device according to certain embodiments of the present invention.

After adhesion of the implant 310 to the patient tissue, other implants, and/or both, the implant 310 is detached from the delivery system 342 and the portion of the lumen 322 associated with the implant 310 is dissociated from the portion of the lumen 322 associated with the delivery system 342. In order to facilitate detachment of the implant 310 from the delivery system 342, as shown in FIG. 9, in certain embodiments of the present invention, a heater 344 is positioned near the lumen 322, for example interior of the lumen 322, at a location near a proximal end 328 of the implant 310. Activation of the heater 344 by the operator severs to sever the lumen 322 and thereby detaches the implant 310 from the delivery system 342. Similar detachment systems are described in U.S. Pat. No. 8,182,506 and U.S. Publication Nos. 2006/0200192 and US2006/052815, all of which are hereby incorporated by reference in their entirety.

Figures 10, 11:
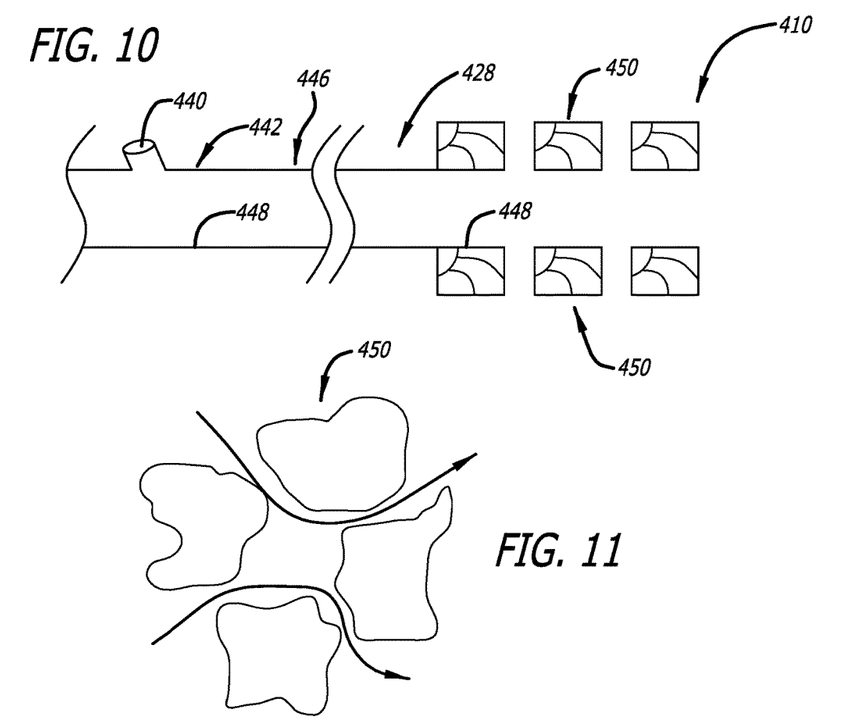
FIG. 10 is a cross-sectional view of a portion of an implantable device according to certain embodiments of the present invention.
FIG. 11 is a magnified view of a flow channel system according to certain embodiments of the present invention.

In another embodiment, with reference to FIGS. 10 and 11, an implant 410 having a multiple flow channel structure 450, such as a honeycomb-like structure, is employed. A proximal portion 428 of the implant 410 is connected to a lumen 448 at a distal portion 446 of a delivery system 442. The lumen 448 extend proximally within the delivery system 442 to an injection port 440, as described previously with respect to the delivery system 342. Adhesive 12 is injected into lumen 448 through the injection port 440, enters an interior volume of the implant 410 and disperses or flows through the complex system of flow channel structure 450 to an exterior surface of the implant 410.

The implant 410 is formed by employing three-dimensional printing techniques. For example, the implant 410 may be formed by vapor deposition or by sintering a powdered metal or plastic over a dissolvable form. The dissolvable form is, for example, shaped in the form of a tubular stent, coil, frame, or similar implantable device formed of a polymer, salt, and/or wax. After vapor deposition or sintering of the powdered metal or plastic over the dissolvable form, the dissolvable form is dissolved with a solvent, water, and/or by heating leaving behind the implant 410 having a structure at least partially complementary to the dissolvable form that comprises the complex flow channel structure 450 spanning from an interior surface to an exterior surface of the implant 410. FIG. 10 shows a magnified view of the flow channel structure 450 of the implant 410.

The lumen 448 is formed, for example, of a polyamide, polyolefin, Teflon, polyamide, PEEK, PET, or the like.

The adhesive 12 employed in the implant 410 is, for example, an adhesive material such as n-butyl cyanoacrylate (nBCA), a protein with adhesive properties such as the secretion of a sandcastle marine worm, or a siloxane system such as that described in Wilson et al., Biomater Sci Polymer Ed. 2005; 16(4): 449-72, which is hereby incorporated by reference in its entirety. In general, it may be advantageous to use an adhesive 12 that is reactive to temperature, pH, salinity, water, or other biological factors in order to facilitate delivery of the implant 410 into the patient's body in a non- or lower- adhesive state. Upon delivery and/or deployment of the implant 410 to the target location, the adhesive strength of the adhesive 12 increases due to, at least in part, the reactivity of the adhesive 12 to a temperature, pH, salinity, water content, or other biological factor(s) present at the target location.

The adhesive 12 can advantageously comprise a radiopaque material such as barium sulfate, tantalum powder, or iodine contrast solution so as to allow an operator to visualize the adhesive as it is delivered through the delivery system 442.

In operation, the implant 410 is delivered to the target location while attached to the delivery system 442. The operator may reposition the implant 410 as needed until the desired location and configuration are achieved. The operator then inject the adhesive 12 into the injection port 440; through the lumen 448; through an interior volume of the implant 410; through the flow channels 450 and onto an exterior surface of the implant 410. Once the adhesive 12 reaches the surface of the implant 410, the adhesive 12 will contact patient tissue, other implants, and/or both and adhere the implant 410 to the patient tissue, other implants, and/or both. Hence, the implant 410 will be held in the target location and the risk of migration of the implant 410 will be reduced.

After adhesion of the implant 410 to the patient tissue, other implants, and/or both, the implant 410 is detached from the delivery system 442. Detachment may be facilitated as described above with respect to the implant 310, e.g. by thermal detachment.

Figure 12:
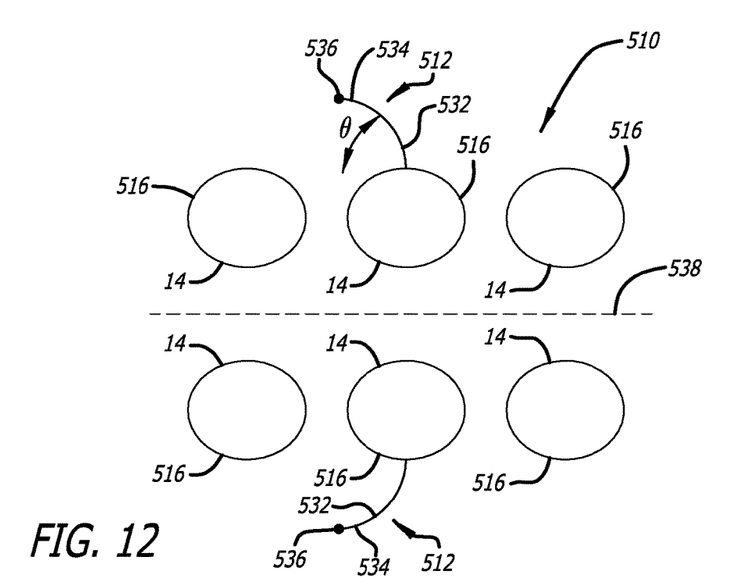
FIG. 12 is a cross-sectional view of a portion of an implantable device with an adhesion promoting structural feature according to certain embodiments of the present invention.
Figure 13:
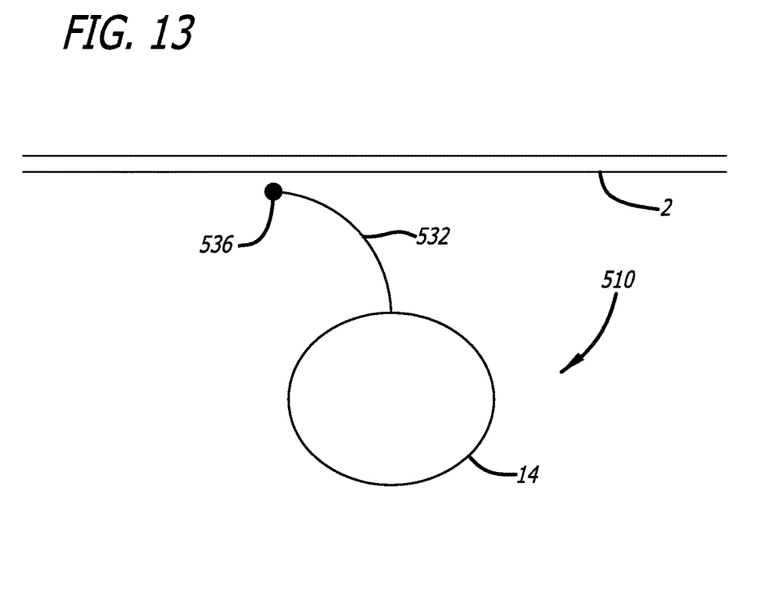
FIG. 13 is a cross-sectional view of a portion of an implantable device with an adhesion promoting structural feature according to certain embodiments of the present invention.
Figure 14:
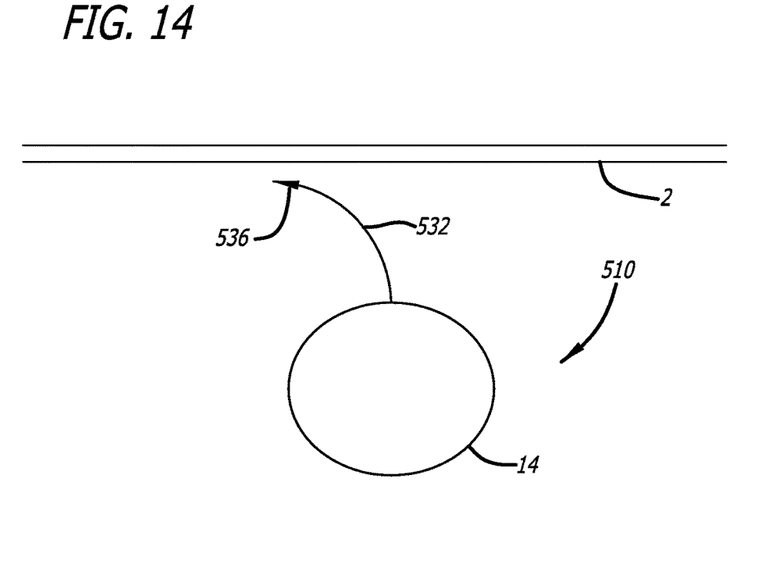
FIG. 14 is a cross-sectional view of a portion of an implantable device with an adhesion promoting structural feature according to certain embodiments of the present invention.

In another embodiment of the present invention, as shown in FIGS. 12-14, an implant 510 employs an adhesive component in the form of adhesion promoting structural features 512. The adhesion promoting structural features 512 employ non-chemical adhesive properties, such as van der Waals forces, to assist in adhering the implant 510 to patient tissue and/or other implants to assist in holding or maintaining the implant 510 at the target location and, thereby, decrease the risk of migration of the implant 510 away from the target location. Such features 512 are further described in U.S. Pat. No. 7,828,982 which is hereby incorporated by reference in its entirety.

In certain embodiments, the structural features 512 are, for example, small protrusions 532 extending from an exterior surface 516 of the implant 512, for example, extending from the exterior surface 516 of a strut 14 of the implant 512. FIG. 12 shows a cross-sectional view of a portion of the implant 510 having a strut 14 employing the protrusion 532 extending from the exterior surface 516. At a distal end 534, the protrusion 532 may, but need not necessarily, employ a tip 536 in order to increase the surface area of the protrusion 532 and, hence the surface area of the implant 510. The tip 536 is, for example, shaped in the form of a sphere, as shown in FIGS. 12 and 13, a spatula or paddle, as shown in FIG. 14, or other regular or irregular shape. For the sake of clarity and by way of example, FIGS. 13 and 14 show cross-sectional views of a single strut 14 of the implant 510 within a patient's vasculature 2. The features 512, i.e. the protrusions 532 and tips 536, are formed, for example, of a metal, alloy, and/or polymer.

The quantity and dispersion of the features 512 employed on the implant 512 are selected based upon the intended application of the implant 512. For example, if the implant 512 is intended for implantation in a relatively high-flow region more features 512 are employed so as to increase the adhesion properties of the implant 512. In contrast, relatively fewer features 512 are employed in a relatively low-flow region where the forces acting upon the implant 512 are relatively lower.

As shown in FIG. 12, the features 512 may, but need not necessarily be, attached to the implant 512 at an angle $\Theta$. The angle $\Theta$ is, for example, determined as an angle of incidence relative to a longitudinal axis 538 of the implant 512. The angle $\Theta$ may be in the range of 5 to 85 degrees, or 25 to 35 degrees.

In certain embodiments, the features 512 attached to the exterior surface 516 of the implant 512 by, for example, laser welding or adhesive bonding. To increase the surface area of the top of the protrusion 532 or the feature 512, a laser can be used to form the tip 536 at the distal end 534 of the protrusion 532. Alternatively, an ultra-violet, UV, curable liquid polymer can be placed at the distal end 534 of the protrusion 532 which will then form the sphere-shaped tip 536 through surface tension and curing.

In certain embodiments, for example, when the protrusion 532 is formed of a ductile material such as platinum or an elastomeric polymer such as an ethylene-octene copolymer, the tip 536 can be mechanically rolled or flattened to form a spatula- or paddle-shaped surface.

In certain embodiments, the features 512 are formed on the surface of the implant 512 by a molding or casting process. For example, the implant 512 is placed in a mold having the features 512 formed therein. A molten metal such as platinum is poured into the mold and hardens as it cools. The mold, for example, could contain features that shape the tips 536 of the protrusions 532, or the tip 536 features could be created by a secondary process as previously described. Alternatively, the implant 512 is placed in the mold and a liquid polymer, for example, a polyimide, dissolved in a solvent or a UV curable polymer, for example, Loctite 349, is poured into the mold and cured by heat to, evaporate the solvent, or UV light. In the present embodiments, the molded features 512 would attach or hold onto the implant 512 either through friction; chemical bonding, if the materials were compatible; or by a secondary process such as laser or resistance welding. Other bonding methods such as, for example, those described in U.S. Pat. No. 7,828,982 may also be employed.

In one illustrative example of the present invention, the implant 512 is a coil intended for to treatment of a neurovascular aneurysm. Other devices to treat larger aneurysms or smaller devices to occlude, for example fallopian tubes or small aneurysms are possible by re-scaling this embodiment. A 0.002 inch platinum alloy wire is wound into a primary coil having a 0.012 inch outer diameter and a 0.008 inch inner diameter. The coil is then wound into a secondary shapes such as a helix or other complex three-dimensional shape, such as a sphere, helix, cage, box, or frames into which other coils can be deployed, as described in U.S. Pat. No. 8,066,036 and U.S. Publication No. US201210041464 which are hereby incorporated by reference in their entirety. For example, the coil can be wound into a secondary shape nominally 6 millimeters in diameter and 25 centimeters in length.

Platinum wires 0.0005-0.004 inches in diameter are cut to lengths 0.001-0.04 inches. More particularly, 0.0002 inch diameter platinum wire is cut in to approximately 0.001 inch lengths. A laser is then used to form a ball-shaped tip 536 of approximately 0.0003 inches in diameter on the end of each platinum wire lengths or protrusions 532. Each ball-tipped protrusion 532 is then laser welded to an exterior surface 516 of the coil at an angle of incidence $\Theta$ of 25 to 35 degrees relative to the longitudinal axis 538 of the coil or implant 512. The protrusions 532 are mounted at 120 degree increments around the longitudinal axis 538 of the coil implant 512 at 1 millimeter increments along the length of the coil implant 512; yielding approximately 750 features 512 on the implant 510.

The coil implant 510 is then attached to a delivery mechanism and delivered through a conventional microcatheter to the target location within the patient. The coil implant 510 can then be repositioned multiple times in, for example, a wide necked aneurysm. The coil implant 510 is detached once the desired deployment configuration is achieved. With prior art implants, there would be a high risk that an implant might migrate into the parent vessel and would, for example, need to be held in place by a stent. However, according to the present invention, the van der Waals forces between the aneurysm wall and the features 512 or the implant 510 will tend to hold the coil implant 510 in place and reduce the risk of migration without using a stent.

According to one embodiment of the present invention, the implants 10, 110, 210, 310, 410, and 510 may employ a combination of the above-described chemical adhesives 12 and the adhesion promoting structural features 512 to achieve the desired adhesive properties.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An implantable device comprising:
    a tubular structure formed of wire struts defining apertures therebetween;
    a porous polymeric covering positioned over the tubular structure;
    a plurality of individual depressions formed into an exterior surface of the wire struts of the tubular structure, an interior volume of each of the individual depressions of the plurality of depressions defined by the polymeric covering positioned over the individual depressions of the plurality of depressions and in communication with at least one pore of the porous polymeric covering, the interior volumes of the individual depressions of the plurality of depressions isolated from a lumen of the tubular structure; and
    a diffusible adhesive component positioned beneath the polymeric covering within the interior volumes of the individual depressions of the plurality of depressions prior to deployment of the implantable device, whereby the diffusible adhesive component is configured to diffuse out from the individual depressions of the exterior surface of the wire struts, through the polymeric covering and past the polymeric covering.

2. The device of claim 1 wherein the diffusible adhesive component comprises a cyanoacrylate.

3. The device of claim 1 wherein the diffusible adhesive component is proteinaceous.

4. The device of claim 1 wherein the diffusible adhesive component comprises a radiopaque material.

5. The device of claim 1 wherein a dimension of the at least one pore of the porous polymeric covering selectively controls a diffusion rate of the diffusible adhesive component through the pores.

6. The device of claim 1 wherein the structure comprises a metallic coil.

7. The device of claim 1 further comprising a temporary sealant formed on the porous polymeric covering.

8. The device of claim 7 wherein the temporary sealant comprises salt or sugar.

9. The device of claim 1 wherein the diffusible adhesive selectively adheres to only a material from which a different implantable device is formed.

10. The device of claim 1 wherein the tubular structure is sized and shaped for deployment in a neurovascular aneurysm.

11. The device of claim 1 wherein the tubular structure comprises an embolic coil.

12. An implantable device comprising:
a tubular support structure formed of wire struts defining apertures therebetween;
a porous polymeric lumen independent of the structure and positioned within an interior of the tubular support structure;
a diffusible adhesive positioned within the porous polymeric lumen; and
a plurality of protrusions extending from an exterior surface of the wire struts that provide an adhesive property to the exterior surface of the implantable device, the individual protrusions of the plurality of protrusions extending from the wire struts at an angle in the range of 25 to 35 degrees relative to a longitudinal axis of the implantable device and having distal sphere-shaped ends formed of a curable polymer.

13. The device of claim 12 wherein the diffusible adhesive is only self-adhering.

14. The device of claim 12 wherein the diffusible adhesive selectively adheres to only a material from which a different implantable device is formed.

15. The device of claim 12 wherein the individual protrusions of the plurality of protrusions comprise distal portions comprising a cross-sectional shape that increases the surface area of the individual protrusions of the plurality of protrusions.

16. The device of claim 12 wherein the tubular structure is sized and shaped for deployment in a neurovascular aneurysm.

17. The device of claim 12 wherein the tubular structure comprises an embolic coil.

* * * * *